US005736520A

United States Patent [19]

Bey et al.

[11] Patent Number: 5,736,520
[45] Date of Patent: Apr. 7, 1998

[54] PEPTIDASE INHIBITORS

[75] Inventors: Philippe Bey; Michael R. Angelastro; Shujaath Mehdi, all of Cincinnati, Ohio

[73] Assignee: Merrell Pharmaceuticals Inc., Cincinnati, Ohio

[21] Appl. No.: 434,959

[22] Filed: May 4, 1995

Related U.S. Application Data

[62] Division of Ser. No. 214,991, Mar. 21, 1994, which is a continuation of Ser. No. 861,775, Apr. 1, 1992, abandoned, which is a continuation-in-part of Ser. No. 750,439, Aug. 20, 1991, abandoned, which is a continuation of Ser. No. 454,803, Dec. 21, 1989, abandoned, which is a continuation-in-part of Ser. No. 439,201, Nov. 20, 1989, abandoned, which is a continuation-in-part of Ser. No. 416,817, Oct. 4, 1989, abandoned, which is a continuation-in-part of Ser. No. 254,762, Oct. 7, 1988, abandoned.

[51] Int. Cl.$^6$ ..................................................... A61K 38/05
[52] U.S. Cl. ..................................................... 514/19; 526/595
[58] Field of Search .......................... 514/18, 19; 526/575

[56] References Cited

U.S. PATENT DOCUMENTS

| | | | |
|---|---|---|---|
| 3,867,364 | 2/1975 | Hamao et al. | 530/331 |
| 4,277,395 | 7/1981 | Bey et al. | 260/112.5 |
| 4,401,594 | 8/1983 | Hamao et al. | 260/112.5 R |
| 4,820,691 | 4/1989 | Patel | 514/19 |
| 5,081,284 | 1/1992 | Higuchi et al. | 560/159 |
| 5,444,042 | 8/1995 | Bartus et al. | 514/2 |
| 5,510,531 | 4/1996 | Higuchi et al. | 564/159 |
| 5,519,048 | 5/1996 | Salituro et al. | 514/419 |

FOREIGN PATENT DOCUMENTS

| | | |
|---|---|---|
| 19392 | 3/1972 | Australia . |
| 0124317 | 11/1984 | European Pat. Off. . |
| 0126009 | 11/1984 | European Pat. Off. . |
| 0128762 | 12/1984 | European Pat. Off. . |
| 0133225 | 2/1985 | European Pat. Off. . |
| 0189203 | 7/1986 | European Pat. Off. . |
| 0195212 | 9/1986 | European Pat. Off. . |
| 0264106 | 4/1988 | European Pat. Off. . |
| 0266950 | 5/1988 | European Pat. Off. . |
| 0281316 | 9/1988 | European Pat. Off. . |
| 0296581 | 12/1988 | European Pat. Off. . |
| 0355572 | 2/1990 | European Pat. Off. . |
| 2490632 | 3/1982 | France . |
| 2537131 | 6/1984 | France . |
| 3000225 | 7/1980 | Germany . |
| 1121257 | 5/1989 | Japan . |
| 0629229 | 4/1994 | Japan . |
| 8400365 | 2/1984 | WIPO . |
| 8404301 | 11/1984 | WIPO . |
| 9211850 | 7/1992 | WIPO . |
| 9212140 | 7/1992 | WIPO . |

OTHER PUBLICATIONS

J.P. Burkhart et al., Tetrahedron Letters, vol. 29, No. 28, 3433–3436 (1988).
S. Mehdi et al., Biochem. and Biophys. Res. Comm., vol. 166, No.2, 595–600 (1990).
Caner et al, Brain Research, 607, pp. 354–356(1993).
Kitagawa et al, Neuroscience vol. 31, No. 2, pp. 401–411, 1989.
Seubert et al, Brain research, 492, (1989) 366–370.
Lee et al, Proc. Natl. Acad. Sci, USA vol. 88, 7233–7237 Aug. 1991 Neurobiology.
M. Angelastro et al., The Journal of Organic Chemistry vol. 54, No. 16, 3913–3916 (1989).
Medhi et al, Biochemical and Biophysical Research Communications vol. 157, No. 3, pp. 1117–1123, (1988).
Bajusz, S. et al., Intl. J. Peptide Protein Res. 12, 1978, pp. 217–221, "Inhibition of Thrombin and Trypsin by Tripeptide Aldehydes".
Mehdi, S. et al, Biochem and Biophys Res Comm, vol.157, No.3, 1117–1123 (1988).
Kozlowski, K. et al., Proc. Natl. Acad. Sci. USA vol. 81, pp. 1135–1139, Feb., 1984, Cell Biology, "Tumor Cell Proteinase Visualization and Quantification Using a Fluorescent Transition–State Analog Probe".
Peptides, Structure & Function (C.M. Deber et al) Proceedings of the American Peptide Symposium, 1985. Hori, H. et al, "Inhibition of Human Leukocyte Elastase, Procine Pancreatic Elastase and Cathepsin G by Peptide Ketones", pp. 819–822.
Peptides, Structure & Function—Proceedings of the American Peptide Symposium, 1985, Galpin, I.J. et al, "A New Approach to the Synthesis of Peptide Aldehyde Inhibitors", pp. 799–802.
Wang K., "Developing selective inhibitors of Calpain", TIPS, Apr., 1990, vol. 11, pp. 139–142.
Bajusz, S. et al., Peptides, Proceedings of the Seventh American Peptide Symposium, Pierce Chemical Company, Rockford, Illinois, 1981, pp. 417–420, "Structure–Activity Relationships Among the Tripeptide Aldehyde Inhibitors of Plasmin and Thrombin".
Bajusz, S. et al., Peptides: Chemistry, Structure and Biology, Proceedings of the Fourth American Peptide Symposium, Ann Arbor Science Publishers Inc., 1975, "Peptide Aldehyde Inhibitors of the Fibrinogen–Thrombin Reaction". pp. 603–608.
Isabel Charles et al, J.C.S, Perkin I, 1980, pp. 1139–1146.
Cs.–Szabo et al, "Specific inhibition of human granulocyte elastise with peptide aldehydes", FEBS, vol. 195, No. 1,2; pp. 265–268, 1986.
Chemical Abstracts, vol. 107, No. 25, 228458u (1987).
Mehdi, S., TIBS 16, pp. 150–153 (Apr., 1991).
Brorson, J., et al, Stroke, vol. 20, No. 7, pp. 1259–1267 (Jul. 1995).

*Primary Examiner*—David Lukton
*Attorney, Agent, or Firm*—Michael J. Sayles

[57] ABSTRACT

This invention relates to analogs of peptidase substrates in which the nitrogen atom of the scissile amide group of the substrate peptide has been replaced by H, an aldehyde, a substituted carbonyl or a substituted malonyl moiety. These analogs of the peptidase substrates provide specific enzyme inhibitors for a variety of proteases, the inhibition of which will have useful physiological consequences in a variety of disease states.

1 Claim, No Drawings

OTHER PUBLICATIONS

Longa, E.Z., et al, Stroke, vol. 20, No. 1, pp. 84–91 (Jan., 1989).

Ito, A. et al., "Peptide Aldehydes Inhibiting Chymotrypsin", Biochemical and Biophysical Research Communications, vol. 49, No. 2, pp. 343–349 (1972).

Thompson, R.C., "Use of Peptide Aldehydes to Generate Transition–State Analogs of Elastase",.Biochemistry, vol. 12, No. 1, pp. 47–51 (1973).

Derwent No. 86–163399 (EP185390, published Jun. 25, 1986).

Derwent No. 82–335432 (FR2490632–A, published Mar. 26, 1982).

Derwent No. 84–129431 (J58164563–A, published Sep. 29, 1983).

Saito, M. et al., "Purification and Structure of Novel Cysteine Proteinase Inhibitors..", Agric. Biol. Chem.. 51(3), pp. 861–868 (1987).

Umezawa, H. et al., "Proteinases in Mammalian Cells and Tissues", Elsevier/–North–Holland Biomedical Press, Barrett (ed), Ch. 15, pp.637–646 (1977).

Ogura, K. et al., "Purification and Structure of a Novel Cysteine Proteinase Inhibitor, Strepine P–1", Agric. Ciol. Chem., 49(3), pp. 799–805 (1985).

Chemical Abstracts 146554g, vol. 80, (1974).

Chemical Abstracts 105:24605p, vol. 106 (1986).

Chemical Abstracts 104:125573m, vol. 104 (1986).

Chemical Abstracts 101:192438x, vol. 101 (1984).

Chemical Abstracts 100:205401m, vol. 100 (1984).

Chemical Abstracts 100:187896v, vol. 100 (1984).

Derwent Publication 89–182787/25, Suntory LTD.

Derwent Publication 86–172210/21, Kawaken Fine Chemical KK.

Sasaki, T. et al., "Inhibitory Effect of DI–and Trippeptidyl Aldehydes..", J. Enzyme Inhibiton, vol. 3, pp. 195–201, (1990).

Chemical Abstracts, vol. 111:174674y (1989).

Chemical Abstracts, vol. 101:23948h PCT Intl. Appl:WP84 00 365 (1984).

Chemical Abstracts, vol. 80:146554g (1973).

Thompson, R.C. "Peptide Aldehydes: Potent Inhibitors of Serine and Cysteine Proteases", Methods Enzymol., vol. 46, pp. 220–225 (1977).

Bajusz, S. et al., Peptides: Chemistry, Structure and Biology, Proceedings of the Fourth American Peptide Symposium, Ann Arbor Science Publishers Inc., "Peptide Aldehyde Inhibitors of the Fibrinogen–Thrombin Reaction" (1975) pp. 603–608.

Cs.–Szabo et al, "Specific inhibition of human granulocyte elastise with peptide aldehydes", FEBS, vol. 195, No. 1, 2; pp. 265–268.

Zhaozhao Li et al, "Peptide α–Keto Ester, α–Keto Amide, and α–Keto Acid Inhibitors of Calpains and Other Cysteine Proteases", J. Med. Chem., vol. 36, pp. 3472–3470 (1993).

Chemical Abstracts 100:114752k, vol. 100, (1984).

Chemical Abstracts 100:19717u, vol. 100 (1984).

Chemical Abstracts 97:19651n, vol. 97 (1982).

Chemical Abstracts 90:99132n, vol. 90 (1979).

Chemical Abstracts 87:196211h, vol. 87 (1977).

Chemical Abstracts 86:5859x, vol. 86 (1977).

Chemical Abstracts 85:105947x, vol. 85 (1976).

Smith, R.A. et al., "Inhibition of Cathepsin B by Peptidyl Aldehydes and Ketones..", Biochemistry 27, pp. 6568–6573 (1988).

Grobelny, D. et al., "Inhibition of Angiotensin Converting Enzyme by Aldehyde and Ketone Substrate Analogues", Biochemistry, vol. 25, No. 5, pp. 1072–1078 (1986).

Thompson, R.C. et al., "Reaction of Peptide Aldehydes with Serine Proteases", Bochemistry, vol. 18, No. 8, pp. 1552–1558 (1979).

Chemical Abstracts 99:170031x, vol. 99 (1983).

Medhi et al, "Inhibition of the Proteolysis of Rat Erythrocyte Membrane Proteins by a Synthetic Inhibitor of Calpain"; Biochemical and Biophysical Research Communications vol. 157, No. 3, pp. 1117–1123, (1988).

Hong et al, "Neuroprotection with a Calpain Inhibitor in a Model of Focal Cerebral Ischemia", Stroke, vol. 25, No. 3, pp. 663–669, (Mar. 1994).

Arlinghaus et al, "Improved posthypoxic recovery with a membrane permable calpain inhibitor", European Journal of Pharmacology, vol. 209, pp. 123–125 (1991).

Tsujinaka, T. et al., "Synthesis of a new cell penetrating calpain hihibitor (calpain)", Biochemical and Biophysical Research Communications vol. 153, No. 3, pp. 1201–1208, (1988).

Baron, B.M., et al, Emergency Management and Critical Care of Stroke (meeting disclosure), Germany, Sep. 1996.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Xaa Xaa Xaa Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Xaa Xaa Xaa Xaa
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Ala Ala Pro Phe
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Ala Ala Pro Phe

1

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:5:

Ala  Ala  Pro  Phe
    1

(2) INFORMATION FOR SEQ ID NO:6:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:6:

Ala  Ala  Pro  Phe
    1

PEPTIDASE INHIBITORS

CROSS REFERENCE TO RELATED APPLICATION

This is a division of application Ser. No. 08/214,991, filed Mar. 21, 1994, which is a continuation of application Ser. No. 07/861,775, filed Apr. 1, 1992, now abandoned which is a continuation in part of application Ser. No. 07/750,439, filed Aug. 20, 1991, now abandoned which is a continuation of application Ser. No. 07/454,803, filed Dec. 21, 1989, now abandoned, which is a continuation in part of application Ser. No. 07/439,201, filed Nov. 20, 1989, now abandoned, which is a continuation in part of application Ser. No. 07/416,817, filed Oct. 4, 1989, now abandoned which is a continuation in part of application Ser. No. 07/254,762, filed Oct. 7, 1988, now abandoned which is herein incorporated by reference.

This invention relates to protease enzyme inhibitors useful for a variety of physiological end-use applications.

In its broad aspects, this invention relates to analogs of peptidase substrates in which the nitrogen atom of the scissile amide group of the substrate peptide has been replaced by H, an aldehyde, a substituted carbonyl or a substituted malonyl moiety. These analogs of the peptidase substrates provide specific enzyme inhibitors for a variety of proteases, the inhibition of which will have useful physiological consequences in a variety of disease states.

In its more specific aspects, this invention relates to derivatives of certain peptidase substrates which are useful in inhibiting Cathepsin G, Cathepsin B, and calpain, the inhibition of which will have useful physiological consequences in a variety of disease states.

Unless otherwise stated the α-amino acids of the foregoing peptidase substrates of this invention are preferably in their L-configuration. A compound of this invention may be in free form, e.g., amphoteric form, or a salt form, e.g., acid addition or anionic salt. A compound may be converted into its salt or base form in an art-known manner, one from another. Preferred salts are trifluoroacetate, hydrochloride, sodium, potassium or ammonium salts, although the scope of salts embraced herein is not limited thereto, the scope being extended to include all of the salts known to be used in the art of peptide chemistry.

As used herein the term "alkyl" includes the straight, branched-chain and cyclized manifestations thereof, particularly such moieties as methyl, ethyl, n-butyl, t-butyl, cyclopropyl, n-propyl, pentyl, cyclopentyl, n-hexyl, n-nonyl, decyl, cyclohexyl and cyclohexylmethyl. The term "butyl" (in its $R_3$ context) includes n-butyl, isobutyl, secondary butyl and t-butyl. The term "aralkyl" includes those aryl moieties attached to a $C_{1-4}$ alkylene. The term "aryl" within the definitions of $R_2$ and $R_3$ includes both carbocyclic and heterocyclic moieties. Preferred aralkyl and aryl moieties are phenyl, benzyl, naphthylmethyl, phenethyl, 2-pyridylmethyl, indolyl, pyridyl, indazolyl, furyl and thienyl are preferred. Other carbocyclics are such fused aryl moieties as pentalenyl, indenyl, naphthalenyl, naphthylmethyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. In the term "—A—$SiR_7R_8R_9$" the alkylene moiety (i.e. "A") is a straight or branched-chain alkylene moiety separating the "$SiR_7R_8R_9$" moiety from the carbon atom to which the "—A—$SiR_7R_8R_9$" radical is attached. Of the $R_7$, $R_8$ and $R_9$ radicals attached to the silicone atom it is preferred that two or three of these radicals be a $C_{1-10}$ lower alkyl radical (preferably methyl or ethyl) and that when one of them contains an aryl radical it is preferred that that radical be a benzyl radical. It is preferred that the alkylene moiety be methylene. Preferred moieties are trimethylsilyl methyl, triethylsilylmethyl, benzyldiethylsilylmethyl, benzyldimethylsilylmethyl, benzylethylmethylsilylmethyl, dimethyl (3-pyridylmethyl) silylmethyl, dimethyl-(3-indolylmethyl) silylmethyl, and the like.

Before further defining and/or illustrating the scope of the peptidase substrate inhibitors of this invention, it may be convenient to state some of the more basic concepts related to peptides. For example, except for proline, all of the α-amino acids found in proteins have, as a common denominator, a free carboxyl group and a free unsubstituted amino group on the α-carbon atom (in proline, since proline's α-amino group is substituted it is really an α-imino acid, but for convenience, it will also be spoken of as an α-amino group). Additionally, each α-amino acid has a characteristic "R-group", the R-group being the side-chain, or residue, attached to the α-carbon atom of the α-amino acid. For example, the R-group residue for glycine is hydrogen, for alanine it is methyl, for valine it would be isopropyl. (Thus, throughout this specification the $R_2$ or $R_4$ moiety is the R-group residue for each indicated α-amino acid). The specific residues—or side chains—of the α-amino acids are all well known to those of ordinary skill in the art.

The recognized abbreviations for the α-amino acids are set forth in Table I.

TABLE I

| AMINO ACID | SYMBOL |
|---|---|
| Alanine | Ala |
| Arginine | Arg |
| Aspargine | Asn |
| Aspartic acid | Asp |
| Asn + Asp | Asx |
| Cysteine | Cys |
| Glutamine | Gln |
| Glutamic acid | Glu |
| Gln + Glu | Glx |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |
| Norvaline | n-Val |
| Norleucine | n-Leu |
| 1-Naphthylalanine | Nal(1) |
| 2-Indolinecarboxylic acid | Ind |
| Sarcosin | Sar |

In those instances wherein the normal R-group residue of an α-amino acid contains an OH radical (e.g. serine, threonine and tyrosine), it is to be understood that such radical can be derivatized. For example, in each of the foregoing 3 instances the OH radical can be converted to an ether. When so-converted, as for example to their methyl ethers, then such radicals will be referred to as O-methyl serine, O-methyl threonine and O-methyl tyrosine, respectively.

In those instances wherein Group K represents an —A—Rz moiety, it is preferred that A represent —C(=O)— and that Rz represent acylsulfonamido, particularly those wherein the acylsulfonamido contains an aryl moiety (preferably phenyl) substituted by a halogen. The preferred —A—Rz moieties being 4-[(4-chlorophenyl)sulfonylaminocarbonyl]phenylcarbonyl, 4-[(4-bromophenyl)sulfonylaminocarbonyl]phenylcarbonyl and 4-[phenylsulfonylaminocarbonyl]phenylcarbonyl (said moieties being abbreviated as ClØ-SAC-Bz, BrØ-SAC-Bz and Ø-SAC-Bz, respectively)

Quite obviously the modifications to the scissile amide bond of the peptidase substrates of this invention presents certain nomenclature difficulties. In order to maintain a general consistency throughout this application the following explanations are offered to obviate any ambiguities relating to the scope and intent of this invention.

In light of the foregoing the compounds of this invention are compounds of the formulae $$R_1NHCHR_2C(O)X \qquad \text{Ib SEQ. ID 1}$$

the hydrates, isosteres or the pharmaceutically acceptable salts thereof, wherein
X is —C(O)R$_3$;
R$_3$ is H, methyl, ethyl, OH, methoxy or ethoxy;
R$_1$ is P$_2$P$_3$P$_4$ or P$_2$P$_3$P$_4$P$_g$, wherein
  P$_g$ is selected from Group K and is preferably Boc, Suc, MeOSuc, 4-ClØSAC-Bz, 4-BrØSAC-Bz or ØSAC-Bz;
  P$_2$ is an α-amino acid of Groups D, E and G, and is preferably Pro;
  P$_3$ is an α-amino acid of Groups E and G, or is deleted, and is preferably Ala;
  P$_4$ is deleted or is an α-amino acid of Groups E and G, and is preferably Ala; and
R$_2$ is the side chain of an α-amino acid of Groups E and F, and is preferably Phe;

$$R_1NHCHR_2C(O)X \qquad \text{In SEQ. ID 2}$$

the hydrates, isosteres or the pharmaceutically acceptable salts thereof, wherein
X is —C(O)R$_3$;
R$_3$ is H, methyl, ethyl, OH, methoxy or ethoxy;
R$_1$ is —P$_2$P$_3$ or —P$_2$P$_3$P$_g$,
  P$_g$ is selectd from Group K and is preferably CBZ, Ac, Box, 4-ClØSAC-Bz or ØSAC-Bz; wherein
  P$_2$ is an α-amino acid of Groups E and F, preferably Phe or Leu;
  P$_3$ is deleted or is an α-amino acid of Groups E and F, preferably Leu; and
R$_2$ is the side chain of Thr,ThrOCH$_2$Ø or an α-amino acid of Groups A or E or is a member of Group J, and is preferably the side chain of Arg or ThrOBz; and $$R_1NHCHR_2C(O)X \qquad \text{Iu}$$

the hydrates, isosteres or the pharmaceutically acceptable salts thereof, wherein
X is H;
R$_1$ is —P$_2$P$_3$P$_g$,
  P$_g$ being a Group K protecting group, preferred protecting groups being Ac, Bz, CBZ, 4-ClØSAC-Bz, 4-BrØSAC-Bz or ØSAC-Bz; wherein
  P$_2$ is the α-amino acid Val;
  P$_3$ is deleted; and
R$_2$ is the side chain of the amino acid Phe.

In the above formulae Ib, In and Iu, the groups referred to are defined as follows:
A is Lys and Arg
D is Pro, Ind
E is Ala, β-Ala, Leu, Ile, Val, n-Val, β-Val, Met, β-Valine, β-Alanine, n-Leu and n-methyl derivatives (β-representing beta)
F is Phe, Tyr, O-Methyl Tyrosine, (3-pyrazolyl)Ala, (4-pyrimidinyl)Ala, Trp, Nal(1), and N-methyl derivatives
G is Gly, Sar
J: is

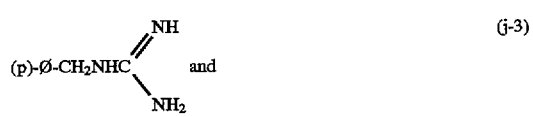

K is Acetyl (Ac), Succinyl (Suc), Benzoyl (Bz), t-Butyloxycarbonyl (Boc), Carbobenzoxy (CBZ), Tosyl (Ts), Dansyl (DNS), Isovaleryl (Ira), Methoxysuccinyl (MeOSuc), 1-Adamantanesulphonyl (AdSO$_2$), 1-Adamantaneacetyl (AdAc), 2-Carboxybenzoyl (2-CBZ), Phenylacetyl, t-Butylacetyl (Tba), bis [(1-naphthyl)methyl]acetyl (BNMA), or —A—Rz wherein

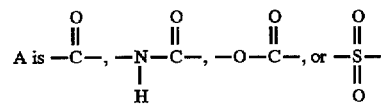

and Rz is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido containing from 1 to 15 carbons, provided that when the acylsulfonamido contains an aryl the aryl may be further substituted by a member selected from fluoro, chloro, bromo, iodo and nitro.

Compounds of this invention which are useful as inhibitors of Cathepsin G are compounds of the formula $$R_1NHCHR_2C(O)X \qquad \text{Ib SEQ. ID 1}$$

the hydrates, isosteres or the pharmaceutically acceptable salts thereof, wherein
X is —C(O)R$_3$,
R$_3$ is H, methyl, ethyl, OH, methoxy or ethoxy, $R_1$ is $P_2P_3P_4$ or $P_2P_3P_4P_g$, wherein $P_g$ is selected from Group K and is preferably Boc, Suc, MeOSuc, 4-ClØSAC-Bz, 4-BrØSAC-Bz or ØSAC-Bz, $P_2$ is an α-amino acid of Groups D, E and G, and is preferably Pro, $P_3$ is an α-amino acid of Groups E and G, or is deleted, and is preferably Ala, $P_4$ is deleted or is an α-amino acid of Groups E and G, and is preferably Ala, and $R_2$ is the residue of an α-amino acid of Groups E and F, and is preferably Phe.

The end-use application of the compounds (Ib) inhibiting Cathepsin G is the same as for human leucocyte inhibitors, including arthritis, gout and emphysema, but also embracing the treatment of glomerulonephritis and lung infestations caused by infections in the lung. For their end-use application, the potency and other biochemical parameters of the enzyme inhibiting characteristics of the compounds of (Ib) is readily ascertained by standard biochemical techniques well known in the art. Actual dose ranges for their specific end-use application will, of course, depend on the nature and severity of the disease state of the patient or animal to be treated as determined by the attending diagnostician. It is to be expected that the general end-use application dose range will be about 0.01 to 10 mg per kg per day for an effective therapeutic effect. Preferred compounds of formula Ib are:

| | |
|---|---|
| Pg-Ala-Ala-Pro-Phe-[C(O)CH₃], | SEQ. ID 3 |
| Pg-Ala-Ala-Pro-Phe-[C(O)OCH₃], | SEQ. ID 4 |
| Pg-Ala-Ala-Pro-Phe-[C(O)H], | SEQ. ID 5 |
| Pg-Ala-Ala-Pro-Phe-[C(O)Et], | SEQ. ID 6 |
| Pg-Val-Pro-Phe-[C(O)CH₃], | |
| Pg-Val-Pro-Phe-[C(O)OCH₃], | | with Pg specifically being Boc, Suc, MeOSuc, 4-ClØSACBz, 4-BrØSACBz or ØSACBz.

Compounds of this invention which are useful as inhibitors of Cathepsin B are compounds of the formula $$R_1NHCHR_2C(O)X \qquad \text{In SEQ. ID 2}$$

the hydrates, isosteres or the pharmaceutically acceptable salts thereof, wherein X is —C(O)R₃, $R_3$ is H, methyl, ethyl, OH, methoxy or ethoxy, $R_1$ is $P_2P_3$ or $P_2P_3P_g$, $P_g$ being a Group K protecting group, preferably CBZ, Ac, Boc, 4-ClØSAC-Bz or ØSAC-Bz, $P_2$ is an α-amino acid of Groups E and F, preferably Phe or Leu, $P_3$ is deleted or is an α-amino acid of Groups E and F, preferably Leu, $R_2$ is the side chain of ThrThrOCH₂Ø or an α-amino acid of Group A or E or is a member of Group J, and is preferably the side chain of Arg or ThrOBz.

The preferred compounds are:

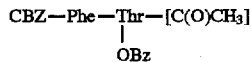

Pg—Phe—Gly—Gly[C(O)CH₃]
(Pg being Ac, Boc, CBZ, 4-Cl or 4-Br-φSACBz or φSACBz).

The compounds of Formula (In) inhibit Cathepsin B and therefore are useful in treating excessive cell growth disease states such as, for example, being useful in treating benign prostate hypertrophy, prostatic carinoma and in treating psoriasis. Additionally, the compounds of (In) are useful as feed additives for cattle. For their end-use application, the potency and other biochemical parameters of the enzyme inhibiting characteristics of the compounds of (In) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

Compounds of this invention which are useful as inhibitors of calpain are compounds of the formula $$R_1NHCHR_2C(O)X \qquad \text{Iu}$$

the hydrates, isosteres or the pharmaceutically acceptable salts thereof, wherein X is H;

$R_1$ is $P_2P_3P_g$, $P_g$ being a Group K protecting group, preferred protecting groups being Ac, Bz, CBZ, 4-ClØSAC-Bz, 4-BrØSAC-Bz or ØSAC-Bz, $P_2$ is Val;

$P_3$ is deleted; and $R_2$ is the residue of thw α-amino acid Phe.

The preferred compound of Formula (Iu) is:

Cbz-Val-Phe-H.

By their inhibition of calpain and cathepsin B proteases the compounds of (Iu) will (a) have an effect on cell motility through the extracellular matrix rendering the compounds useful for treating cancer metastases; (b) have long term changes in regulatory proteins (e.g. down-regulation of protein kinase C and breakdown of the cytoskeleton causing secondary effects on platelet activation such as (for enhancing clot formation) leukocyte degranulation (for treating inflammation and immunological diseases, e.g. arthritis, emphysema, multiple sclerosis, and systemic lupus); (c) have a general inhibition of intracellular proteolysis, particularly for muscle cells, causing secondary effect on ischemia/reperfusion cell death, thereby rendering the compounds useful for treating stroke and heart attacks; and (d) will aid in blocking the lysis of red blood cells rendering the compounds useful in the treatment of conditions associated with excessive hemolysis such as in Sickle cell anemia and in kidney dialysis. It is to be expected that the end-use application dose range will be about 0.01 to 10 mg per kg of body weight per day for an effective therapeutic effect.

The preparation of the compounds of this invention may be effected by standard chemical processes analogously known in the art. The processes are depicted in Reaction Schemes A, B and C, and described as follows.

In those instances wherein X is H or C(O)R₃, the compounds are prepared according to processes generically depicted in Reaction Scheme A.

Reaction Scheme A

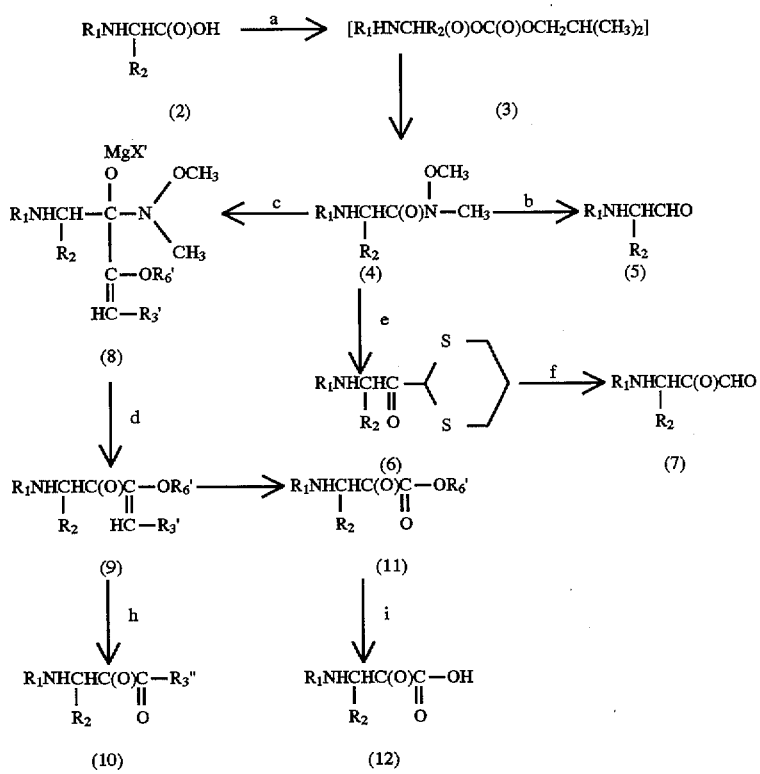

wherein X' is chloro or bromo, $R_3'$ is H or methyl, $R_3"$ is methyl or ethyl, $R_6'$ is methyl or ethyl and $R_1$ and $R_2$ are as previously defined.

In effecting the processes of the foregoing reaction scheme, the starting materials (2) are subjected to process step (a) which is initiated by anionizing the starting material with a base, preferably N-methyl morpholine, triethylamine (TEA), diisopropylethylamine (DIEA) or other suitable amines. Preferably the anion is formed using excess quantities of the amine, stirring the mixture at about −15° C. to 10° C., preferably 0° C. Addition of an equivelent amount of isobutylchloroformate with cooling at about −20° C. forms an in situ mixed anhydride (3). (Other equivalently functioning peptide coupling agents, such as diethylcyanophosphonate, DCC, BOP reagents, BOP chloride, may be used in place of isobutylchloroformate.) Addition of molar equivalent amounts of N,O-dimethylhydroxylamine to the activated in situ intermediate (3) yields a dimethylhydroxamic acid derivative (i.e. an N-methyl-N-methoxy amide) of Formula 4. This step, as well as reaction steps (b) and (g), are conducted under an inert atmosphere (argon or nitrogen) under anhydrous conditions.

The hydroxamic derivatives (4) may be chemically reduced step (b) using standard Castro reduction conditions, e.g., lithium aluminum hydride in THF at 0° C. or other equivalently functioning reductions, to yield the desired aldehydes (5), or they may be subjected to the reaction conditions of steps (c) and (d) to form compounds 9. Step (c) entails a Grignard reaction using standard reaction conditions such as contacting the reactants together in an inert solvent, preferably tetrahydrofuran, at temperatures of about −20° C. to 0° C. The Grignard is freshly prepared from an organo lithium species, e.g., t-butyl lithium added to ethyl vinyl ether which is converted to an ethyl vinyl ether Grignard reagent by reaction with magnesium bromide using standard procedures well known in the art. The hydroxamic derivatives (4) are added to the Grignard reagent to form an in situ Grignard complex (8) which, by Step (D), is converted to an α-keto vinyl ether (9), said α-keto vinyl ether being converted by treatment with hydrochloric acid in a dioxane-water mixture or any other inert solvent such as tetrahydrofuran, to the desired diketones of Formula 10.

To obtain the desired α-keto aldehyde of Formula 7, the hydroxamic acid derivatives 4 may be subjected to a nucleophilic attack by 2-metallo-1,3-dithiane according to the techniques of D. Seebach and E. J. Corey [J. Org. Chem., Vol. 40, page 231, (1975)] to form compounds 6. Preferably 2-metallo-1,3-dithiane is formed by addition of a slight excess (5%) of n-butyllithium to a solution of 1,3-dithiane in tetrahydrofuran cooled at −40° C. To this solution is added ½ equivalent of derivatives 4 in an inert solvent and the mixture is stirred at a temperature of about −20° C. to 20° C. for 1 to 24 hours. The thioketal derivatives 6 may be hydrolyzed to the desired ketoaldehyde derivatives 7 by following standard procedures [J. Org. Chem., 36, 3553 (1971)] such as the use of Lewis acids, $HgCl_2$, or $BF_3$ etherate, in presence of insoluble base, HgO or $CO_3CO_2$ in aqueous polar solvents, or the use of oxidative agent, i.e. N-halosuccinimide in aqueous acetonitrile.

To obtain the desired α-keto esters, the ethyl vinyl ethers of Formula 9 are subjected to an ozonolysis (g) which entails treatment with ozone in methylene chloride or other inert solvents at −78° C. under an inert atmosphere ($N_2$ or Ar) to form an in situ ozonide which is converted by treatment with dimethylsulfide to form the desired α-keto esters of Formula 11. These compounds (11) may then be subjected to an acid or base catalyzed hydrolysis (preferably LiOH) to produce compounds of Formula 12.

Of course, in those instances wherein it is more convenient for synthesis compounds wherein $R_1$ is a protecting group (preferably BOC) may be prepared by analogous chemical processes and then such compounds would be subjected to solid-phase sequential and block phase synthetic techniques in order to prepare compounds having the requisite $R_1$ moiety.

The solid phase sequential procedure can be performed using established automated methods such as by use of an automated peptide synthesizer. In this procedure an amino protected amino acid is bound to a resin support at the carboxy terminal end, the amino acid is deprotected at the amino position at which a peptide linkage is desired, the amino group neutralized with a base and the next amino protected amino acid in the desired sequence is coupled in a peptide linkage. The deprotection, neutralization and coupling steps are repeated until the desired polypeptide is synthesized. The compounds of the present invention are thus synthesized from their carboxy terminal end to their amino terminal end. The amino protected amino acid can be a conventional amino acid, a derivative or isomer thereof, or a spacer group. The resin support employed can be any suitable resin conventionally employed in the art for the solid phase preparation of polypeptides. The preferred resin is polystyrene which has been cross-linked with from about 0.5 to about 3% divinyl benzene, which has been either benzhydrylamidated, chloromethylated or hydroxymethylated to provide sites for amide or ester formation with the initially introduced amino protected amino acid.

An example of a hydroxymethyl resin is described by Bodansky et al. [Chem. Ind. (London) 38, 1597–98 (1966)]. The preparation of chloromethyl and benzhhydrylamine resins are described by Stewart et al. ["Solid Phase Peptide Synthesis", 2nd Edition, Pierce Chemical Co., Rockford, Ill. (1984), Chapter 2, pp. 54–55]. Many of these resins are available commercially. In general, the amino protected amino acid which is desired on the carboxy-terminal end of the peptide is bound to the resin using standard procedures and practices as are well known and appreciated in the art. For example, the amino protected amino acid can be bound to the resin by the procedure of Gisin [Helv. Chem. Acta, 56, 1476 (1973)]. When it is desired to use a resin containing a benzhydrylamine moiety as the resin binding site an amino protected amino acid is coupled to the resin through an amide linkage between its α-carboxylic acid and the amino moiety of the resin. This coupling is effected using standard coupling procedures as described below. Many resin-bound amino acids are available commercially.

The α-amino protecting group employed with each amino acid introduced into the polypeptide sequence may be any such protecting group known in the art. Among the classes of amino protecting groups contemplated are: (1) acyl type protecting groups such as formyl, trifluoroacetyl, phthalyl, p-toluenesulfonyl (tosyl), benzenesulfonyl, nitrophenylsulfenyl, tritylsulfenyl, o-nitrophenoxyacetyl, and α-chlorobutyryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α-, α-dimethyl-3,5-dimethoxybennzyloxycarbonyl and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thio urethane type protecting groups such as phenylthiocarbonyl; (6) alkyl type protecting groups such as triphenylmethyl (trityl) and benzyl (Bzl); (7) trialkylsilane protecting groups such as trimethylsilane. The preferred α-amino protecting group is tert-butyloxycarbonyl (Boc). The use of Boc as an α-amino protecting group for amino acids is described by Bodansky et al. in "The Practice of Peptide Synthesis", Springer-Verlag, Berlin (1984), p. 20.

Following the coupling of the amino protected amino acid to the resin support, the α-amino protecting group is removed using any suitable procedure such as by using trifluoroacetic acid, trifluoroacetic acid in dichloromethane, or HCl in dioxane. The deprotection is carried out at a temperature of between 0° C. and room temperature. Other standard cleaving reagents may be used for removal of specific amino protecting groups under conditions well known and appreciated in the art.

After removal and neutralization of the α-amino protecting group the next desired amino-protected amino acid is coupled through a peptide linkage. This deprotection, neutralization and coupling procedure is repeated until a polypeptide of the desired sequence is obtained. Alternatively, multiple amino acid groups may be coupled by the solution method prior to coupling with the resin supported amino acid sequence.

The selection and use of an appropriate coupling reagent is within the skill of the ordinary practitioner in the art. Particularly suitable coupling reagents where the amino acid to be added is Gln, Asn, or Arg are N,N-dicyclohexylcarbodiimide and 1-hydroxybenzotriazole. The use of these reagents prevents nitrile and lactam formation. Other coupling agents are (1) carbodiimides (e.g., N,N-dicyclohexylcarbodiimide and N-ethyl-N'-(γ-dimethylaminopropylcarbodiimide); (3) ketenimines; (4) isoxazolium salts (e.g., N-ethyl-5-phenylisoxazolium-3-sulfonate); (5) monocyclic nitrogen containing heterocyclic amides of aromatic character containing one through four nitrogens in the ring such as imidazolides, pyrazolides, and 1,2,4-triazolides (specific heterocyclic amides that are useful include N,N-carbonyldiimidazole and N,N-carbonyl-di-1,2, 4-triazole); (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-o-Ala-Boc); (8) nitrogen containing heterocyclic compounds having a hydroxy group on one ring nitrogen (e.g., N-hydroxyphthalimide, N-hydroxysuccinimide, and 1-hydroxybenzotriazole). Other activating reagents and their use in peptide coupling are described by Kapoor [J. Pharm. Sci., 59, 1–27 (1970)]. The generally preferred coupling method for the amino acids used in the present invention is the use of the symmetrical anhydride as the coupling agent.

The preferred coupling method for Gln, Asn and Arg is to react the protected amino acid, or derivatives or isomers thereof, with N,N-dicyclohexylcarbodiimide and 1-hydroxybenzotriazole (1:1) in N,N-dimethylformamide (DMF) in the presence of the resin or resin-bound amino acid or peptide. The preferred coupling method for other amino acids involves reacting the protected amino acid, or derivative or isomer thereof, with N,N-dicyclohexylcarbodiimide in dichloromethane to form the symmetrical anhydride. The symmetrical anhydride is then introduced into the solid phase reactor containing the resin or resin-bound amino acid or peptide, and the coupling is carried out in a medium of (DMF), or dichloromethane, or DMF: dichloromethane (1:1). A medium of DMF is preferred. The success of the coupling reaction at each stage of the synthesis is monitored by a ninhydrin test as described by Kaiser et al. [Analyt. Biochem. 34, 595 (1970)]. In cases where incomplete coupling occurs, the coupling procedure is repeated. If the coupling is still incomplete, the deprotected amine is capped with a suitable capping reagent to prevent its continued synthesis. Suitable capping reagents and the use thereof are well known and appreciated in the art. Examples of suitable capping reagents are acetic anhydride and acetylimidazole as described by Stewart et al. ["Solid Phase Peptide Synthesis", 2nd Ed., Pierce Chemical Co., Rockford, Ill. (1984), Chapter 2, p. 73].

After the desired amino acid sequence has been obtained, the peptide is cleaved from the resin. This can be effected by procedures which are well known and appreciated in the art, such as by hydrolysis of the ester or amide linkage to the resin. It is preferred to cleave the peptide from the benzhydrylamine resin with a solution of dimethyl sulfide, p-cresol, thiocresol, or anisole in anhydrous hydrogen fluoride. The cleavage reaction is preferably carried out at temperatures between about 0° C. and about room temperature, and is allowed to continue preferably from between about 5 minutes to about 5 hours.

As is known in the art of solid phase peptide synthesis, many of the amino acids bear side chain functionalities requiring protection during the preparation of the peptide. The selection and use of an appropriate protecting group for these side chain functionalities is within the ability of those skilled in the art and will depend upon the amino acid to be protected and the presence of other protected amino acid residues in the peptide. The selection of such a side chain protecting group is critical in that it must not be removed during the deprotection and coupling steps of the synthesis. For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine, homocysteine, penicillamine and the like or derivatives thereof; benzyl (Bzl) or cyclohexyl ester moieties can be used to protect carboxylic acid side chains of amino acids such as Asp, Glu; a benzyl (Bzl) ether can be used to protect the hydroxy containing side chains of amino acids such as Ser and Thr; and a 2-bromocarbobenzoxy (2Br-Z) moiety can be used to protect the hydroxy containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin.

The compounds are then isolated and purified by standard techniques. The desired amino acids, derivatives and isomers thereof can be obtained commercially or can be synthesized according to standard practices and procedures well known in the art.

The following specific examples are given to illustrate the preparation of this invention although the scope of compounds is meant to be limiting to the scope of compounds embraced by formula I.

EXAMPLE 1

Carbamic acid, [1-[[[3-ethoxy-2-oxo-1-(phenylmethyl)-3-butenyl]amino]carbonyl]-2-methylpropyl]-, phenylmethyl ester A solution of ethylvinylether (3 ml) in tetrahydrofuran (20 ml) was cooled to −78° C. and t-butyllithium (10 ml, 17 mmol, 1.7M in pentane) was added. The mixture was warmed to 0° C. and stirred 0.75 h. To the mixture magnesium bromide etherate (4.38 g, 17 mmol) was added followed by stirring for 5 min. To the mixture, a solution of L-phenylalaninamide, N-[(phenylmethoxy)carbonyl]-L-valyl-N-methoxy-N-methyl (1.75 g, 3.98 mmol) dissolved in tetrahydrofuran (5 ml) was addded and the mixture was stirred for 1.5 h. The reaction mixture was poured into dil. $NH_4Cl$ and the aqueous phase was extracted with ethylacetate (3×75 ml). The combined organic extracts were washed with dil. $NaHCO_3$ and dried over $Na_2SO_4$. The removal of solvent in vacuo yielded 1.7 g crude product. The product was purified by recrystallization from 40% EtOAc/hexane-recovery 1.1 g.

EXAMPLE 2

Carbamic acid, [1-[[[2,3-dioxo-1-(phenylmethyl)-butyl]amino]carbonyl]-2-methylpropyl]-, phenylmethyl ester To a solution of carbamic acid, [1-[[[3-ethoxy-2-oxo-1-(phenylmethyl)-3-butenyl]amino]carbonyl]-2-methylpropyl]-, phenylmethyl ester, stereoisomer (300 mg) in 5:1 dioxane/$H_2O$ (10 ml), conc. HCl was added. The mixture was stirred for 24 h at room temperature, poured into dil. $NaHCO_3$ and extracted with ethyl acetate (3×50 ml). The combined extracts were dried over $Na_2SO_4$ and the removal of solvent in vacuo gave 330 g of crude product. The product was purified by flash chromatography (30% EtOAc/hexane) to yield 210 mg of the expected product.

EXAMPLE 3

L-Phenylalaninamide, N-[(phenylmethoxy)carbonyl]-L-valyl-N-methoxy-N-methyl

To a suspension of L-phenylalanine, N-[N-[(phenylmethoxy)carbonyl]-L-valyl] (2.5 g, 6.25 mmol) in methylene chloride (25 ml), N-methylmorpholine (1.5 ml) was added. The solution was cooled to −15° C., followed by the addition of isobutylchloroformate (0.8 ml). The solution was stirred for 20 min and N'O-dimethylhydroxylamine HCl (1.0 g) was added. The solution was stirred at −15° C. for 1 h, allowed to warm to room temperature and stirred for an additional 3 h. The reaction mixture was poured into dil. $NaHCO_3$ and extracted with ethyl acetate (3×75 ml). The combined extracts were dried over $Na_2SO_4$, the solvent was removed in vacuo and the crude product was loaded onto a silica gel column for purification. The expected product was eluted with 75% EtOAc/hexane to yield 1.8 g.

EXAMPLE 4

L-N-(Phenylmethoxy)carbonyl-phenylalaninamide-N'-methoxy-N'-methyl

To a solution of L-N-(phenylmethoxy)carbonyl-phenylalanine (25 g, 0.084 mol) in methylene chloride (300 ml), N-methylmorpholine (18.4 ml, 0.167 mol) was added. The mixture was cooled to −15° C. and isobutylchloroformate (10.8 ml, 83.6 mmol) was added. The mixture was stirred at −15° C. for 15 min followed by the addition of N,O-dimethylhydroxylamine HCl (8.5 g). The mixture was stirred at −15° C. for 1 h, allowed to warm to room temperature and stirred for 3 h. The reaction mixture was poured into $H_2O$ (300 ml) and the aqueous phase was extracted with methylene chloride (2×150 ml). The combined organic extracts were dried over $Na_2SO_4$, the volume was reduced to 100 ml and filtered through silica gel (2 inch). The silica gel was washed with methylene chloride (200 ml) and the solvent was removed from the combined filtrates to yield 26.14 g of the expected product.

EXAMPLE 5

2-Ethoxy-5-phenyl-4-[(phenylmethoxy)carbonyl]amino-3-oxo-1-pentene

A solution of ethylvinylether (1.38 ml, 14.5 mmol) in tetrahydrofuran (40 ml) was cooled to −78° C. and t-butyllithium (8.53 ml, 14.5 mmol, 1.7M in pentane) was added. The mixture was warmed to 0° C., stirred for 45 min, cooled to −30° C. and magnesium bromide etherate (3.74 g, 14.5 mmol) was added. The mixture was warmed to 0° C. over a 15 min period followed by the addition of L-N-(phenylmethoxy)carbonyl-phenylalaninamide-N'-methoxy-N'-methyl (1.0 g, 2.9 mmol). The mixture was allowed to warm to room temperature and stirred for 3 h. The mixture was poured into dil. $NH_4Cl$ and extracted with diethylether (3×100 ml). The combined extracts were dried over $Na_2SO_4$ and the removal of solvent yielded 0.8 g crude product. The crude product (600 mg) was loaded onto silica gel and elution with 20% EtOAc/hexane yielded 410 mg of the expected product.

EXAMPLE 6

2,3-Dioxo-5-phenyl-4-[(phenylmethoxy)carbonyl]amino pentane

To a solution of 2-ethoxy-5-phenyl-4-[(phenylmethoxy)carbonyl]amino-3-oxo-2-penten (100 mg) in methanol (10 ml), concentrated HCl (0.1 ml) was added. The mixture was stirred for 24 h, poured into $H_2O$ and $NaHCO_2$ was added. The aqueous phase was extracted with ethyl acetate (3×50 ml). The combined organic extracts were dried over $Na_2SO_4$ and removal of solvent in vacuo yielded 95 mg crude product. The product was purified by flash chromatography (30% EtOAc/hexane) to yield 65 mg of the expected product.

EXAMPLE 7

Carbamic acid, [5-[[(1,1-dimethylethoxy)carbonyl]amino]-6-(methoxymethylamino)-6-oxohexyl], phenylmethyl ester A solution of L-lysine, $N^2$-[(1,1-dimethylethoxy)carbonyl]$N^6$-[(phenylmethoxy)carbonyl] (10 g, 26.3 mmol) in methylene chloride was cooled to 0° C. and diisopropylethylamine (9.15 ml) was added. To the mixture isobutylchloroformate (3.4 ml, 26.3 mmol) was added, followed by cooling to −15° C., stirring for 15 min, followed by the addition of N,O-dimethylhydroxylamine HCl (2.7 g). The mixture was stirred at −15° C. for 2 h, allowed to warm to room temperature and stirred for 18 h. The reaction mixture was poured into $H_2O$ (200 ml) and extracted with methylene chloride (2×150 ml). The combined extracts were dried over $MgSO_4$ and removal of solvent in vacuo yielded 13.5 g crude product. The crude product (3.0 g) was loaded onto silica gel for purification. Elution with 50% EtOAc/hexane afforded 2.01 g of the expected product.

EXAMPLE 8

Carbamic acid, [5-[(1,1-dimethylethoxy)carbonyl]amino]-7-ethoxy-6-oxo-7-octenyl], phenylmethyl ester A solution of ethylvinylether (2 ml) in tetrahydrofuran was cooled to −78° C. and t-butyllithium (12 ml, 20.4 mmol, 1.7M in pentane) was added. The mixture was stirred at −78° C. for 1 h, warmed to 0° C. and stirred for 1 h. To the mixture magnesium bromide etherate (5–33 g, 20.6 mmol) was added followed by stirring for 15 min and then the addition of carbamic acid, [5-[[(1,1-dimethylethoxy)carbonyl]amino]-6-(methoxymethylamino)-6-oxohexyl]-, phenylmethyl ester (1.75 g). The mixture was stirred for 1 h at 0° C., poured into dil. $NH_4Cl$ and extracted with ethyl acetate (3×100 ml). The combined organic extracts were washed with $NaHCO_3$, $H_2O$ and dried over $Na_2SO_4$. The solvent was removed in vacuo and the crude product was loaded onto silica gel for purification. Elution with 50% EtOAc/hexane afforded 0.97 g of the expected product.

EXAMPLE 9

7-(Phenylmethoxycarbonylamino)-3-[(1,1-dimethylethoxy)carbonylamino]-2-oxo-heptanoic acid ethyl ester A solution of carbamic acid, [5-[(1,1-dimethylethoxy)carbonyl]amino]-7-ethoxy-6-oxo-7-octenyl], phenylmethyl ester, (2S) (100 mg) in $CH_2Cl_2$/methanol (25/1 ml) was cooled to −78° C. and ozone was bubbled through until the appearance of a blue color. Oxygen was bubbled through to dissipate excess ozone followed by the addition of dimethylsulfide (100 mg). The mixture was poured into $H_2O$ and extracted with $CH_2Cl$ (2×40 ml). The combined extracts were dried over $Na_2SO_4$. The solvent was removed in vacuo and the crude product was loaded onto silica gel for purification. Elution with 50% EtOAc/hexane yielded 45 mg of the expected product.

EXAMPLE 10

L-Phenylalaminal, N[(phenylmethoxy)carbonyl]-L-valyl

A solution of L-phenylalaninamide, N[(phenyl-methoxy)carbonyl]-L-valyl-N'-methoxy-N'-methyl (3 g, 6.8 mol) in tetrahydrofuran (50 ml) was cooled to 0° C. and LAH (250 mg) was added. The mixture was stirred at 0° C. for 30 min and quenched by the addition of 10% potassium hydrogen sulfate. The mixture was poured into $H_2O$ (400 ml) and the aqueous phase was extracted with ethyl acetate (3×150 ml). The combined organic extracts were dried over $MgSO_4$ and the solvent was removed in vacuo. The crude product was loaded onto silica gel for purification and the product was eluted with 55% EtOAc/hexane to yield 1.6 g of the expected compound.

EXAMPLE 11

2-[L-N-(Phenylmethoxycarbonyl)amino)phenylalaninyl]-1,3-dithiane

To a solution of 1,3-dithiane (6.0 g, 0.05 mol) in tetrahydrofuran (150 ml) at −30° C., n-butyllithium (27.5 ml of 2.0M n-butyllithium in pentane, 0.055 mol) is added. The mixture is stirred for 2 h and L-N-[(phenylmethoxy)carbonyl]-N'-methoxy-N'-methylphenylalaninamide (3.42 g, 10.0 mmol) is dissolved in tetrahydrofuran (15 ml) and added. The reaction mixture is stirred at 0° C. for 24 h, poured into $H_2O$ and extracted with diethyl ether. The combined organic extracts are washed with $H_2O$, saturated NaCl and dried over $Na_2SO_4$. The solvent is removed in vacuo and the crude product is purified by flash chromatography on silica gel.

EXAMPLE 12

3-[((Phenylmethoxy)carbonyl)amino]-4-phenyl-2-oxobutyraldehyde

To a solution of 2-[L-N-(phenylmethoxycarbonyl)amino) phenylalaninyl]-1,3-dithiane (387 mg, 1.0 mmol) in a mixture of acetonitrile/H$_2$O (9:1) (10 ml), bis(trifluoroacetoxy) iodobenzene (644 mg, 1.5 mmol) is added. The reaction mixture is stirred at room temperature until completion as determined by thin layer chromatography, poured into saturated aqueous sodium bicarbonate and extracted with diethyl ether. The combined organic extracts are dried over Na$_2$SO$_4$, the solvent is removed in vacuo and the crude product is purified by flash chromatography on silica gel.

EXAMPLE 13

2-Oxo-3-[((Phenylmethoxy)carbonyl)amino]-4-phenylbutyric acid

2-Oxo-3-[((phenylmethoxy)carbonyl)amino]-4-phenylbutyric acid ethyl ether (355 mg, 1.0 mmol) in a mixture of dioxane/H$_2$O is dissolved (10:1, 20 ml) and LiOH (72 mg, 3.0 mmol) is added. The mixture is stirred for 5 h, poured into dilute HCl and extracted with diethyl ether. The combined organic extracts are dried over Na$_2$SO$_4$ and the solvent removed in vacuo. The crude product is purified by flash chromatography on silica gel.

EXAMPLE 14

4-Hydroxy-6-phenyl-5-[((phenylmethoxy)carbonyl)amino]-3-oxohexanoic Acid Ethyl Ester A solution of 2-hydroxy-4-phenyl-3-[((phenylmethoxy)carbonyl)amino]butanoic acid, N-methoxy-N-methylamide (372 mg, 1.0 mmol) in tetrahydrofuran is cooled to -78° C. and ethyl lithioacetate (72 mg, 3.0 mmol) is added. The solution is stirred at -78° C. for 1 hour, allowed to warm to room temperature, stirred for 1 hour and poured into dilute HCl. The product is extracted by ethyl acetate (3×150 ml) and the combined organic extracts are washed with NaHCO$_3$, dried over Na$_2$SO$_4$ and the solvent removed in vacuo. The crude product is purified by flash chromatography on silica gel.

EXAMPLE 15

3,4-Dioxo-5-[((phenylmethoxy)carbonyl)amino]-6-phenylhexanoic Acid Ethyl Ester

A solution of 4-hydroxy-6-phenyl-5-[((phenylmethoxy)carbonyl)amino]-3-oxohexanoic acid ethyl ester (397 mg, 1.0 mmol) is dissolved in acetonitrile (15 ml) and the Dess-Martin periodinane (1.27 g, 3.0 mmol)) is added. To the mixture trifluoroacetic acid (342 mg, 3.0 mmol) is added and the mixture is stirred for 48 h. The solvent is removed in vacuo and EtOAc (100 ml) is added, followed by the addition of a solution of NaHCO$_3$ (0.80 g) and Na$_2$S$_2$O$_3$ (1.41 g) in H$_2$O (25 ml). The organic layer is separated and the aqueous phase extracted with ethyl acetate. The combined extracts are dried over Na$_2$S$_2$O$_3$ and the solvent is removed in vacuo. The product is purified by flash chromatography on silica gel.

EXAMPLE 16

3,4-Dioxo-5-[((phenylmethoxy)carbonyl)amino]-6-phenylhexanoic Acid

To a solution of 3,4-dioxo-5-[((phenylmethoxy)carbonyl)amino]-6-phenylhexanoic acid ethyl ester (400 mg, 1.0 mmol) in dioxane/H$_2$O (10:1), lithium hydroxide (72 mg, 3.0 mmol) is added. The mixture is stirred for 3 h, the solvents are removed in vacuo and the crude product is used without purification.

EXAMPLE 17

N-[3,4-Dioxo-5-(((phenylmethoxy)carbonyl)amino))-6-phenylhexanoyl]glycinamide

To a solution of 3,4-dioxo-5-[((phenylmethoxy)carbonyl) amino]-6-phenylhexanoic acid (370 mg, 1.0 mmol) in methylene chloride (300 ml) is added N-methylmorpholine (0.30 g, 3.0 mmol). The mixture is cooled to -15° C., and isobutylchloroformate (136 mg, 1.0 mmol) is added. The mixture is stirred at -15° C. for 15 minutes followed by the addition of N,O-dimethylhydroxylamine hydrochloride (194 mg, 1.0 mmol). The mixture is stirred at -15° C. for 1 hour, allowed to warm to room temperature, and stirred for 3 h. The reaction mixture is poured into H$_2$O (300 ml), and the aqueous phase is extracted with methylene chloride (2×150 ml). The combined organic extracts are dried over Na$_2$SO$_4$, reduced in volume to 100 ml, and filtered through silica gel (2 in.). The solvent is removed in vacuo to give the crude product which is purified by flash chromatography.

The foregoing describes in detail the generic and specific aspects of the scope of the invention as well as the manner of making and using the invention. In addition thereto, although such procedures are known in the art, references setting forth state of the art procedures by which the compounds may be evaluated for their biochemical effects is also included herein. Cathepsin G, cathepsin B and calpain can be assayed and effects of inhibitors are assessed in vitro by spectroscopic techniques.

By following the technique referred above, as well as by utilization of other known techniques, as well as by comparison with compounds known to be useful for treatment of the above-mentioned disease states, it is believed that adequate material is available to enable one of ordinary skill in the art to practice the invention. Of course, in the end-use application of the compounds of this invention, the compounds are preferably formulated into suitable pharmaceutical preparations such as tablets, capsules or elixers, for oral administration or in sterile solutions or suspensions for parenteral administration. The compounds of this invention can be administered to patients (animals and human) in need of such treatment in a dosage range of 0.01–10 mg per kg of body weight per day. As stated above, the dose will vary depending on severity of disease, weight of patient and other factors which a person skilled in the art will recognize.

Typically the compounds described above are formulated into pharmaceutical compositions as discussed below.

About 10 to 500 mg of a compound or mixture of compounds of Formula I or a physiologically acceptable salt is compounded with a physiologically acceptable vehicle, carrier, excipient, binder, perservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for inhibiting calpain in a patient in need thereof which comprises administering to the patient a therapeutically effective amount of a compound of the formula $$Pg\text{-}Val\text{-}NHCH(R_2)(C=O)\text{---}H$$

a hydrate or a pharmaceutically acceptable salt thereof, wherein Pg is Cbz and $R_2$ is the side chain of the α-amino acid Phe.

* * * * *